Jan. 30, 1940. C. SALBACH Plant Pat. 358
GLADIOLUS
Filed March 23, 1939
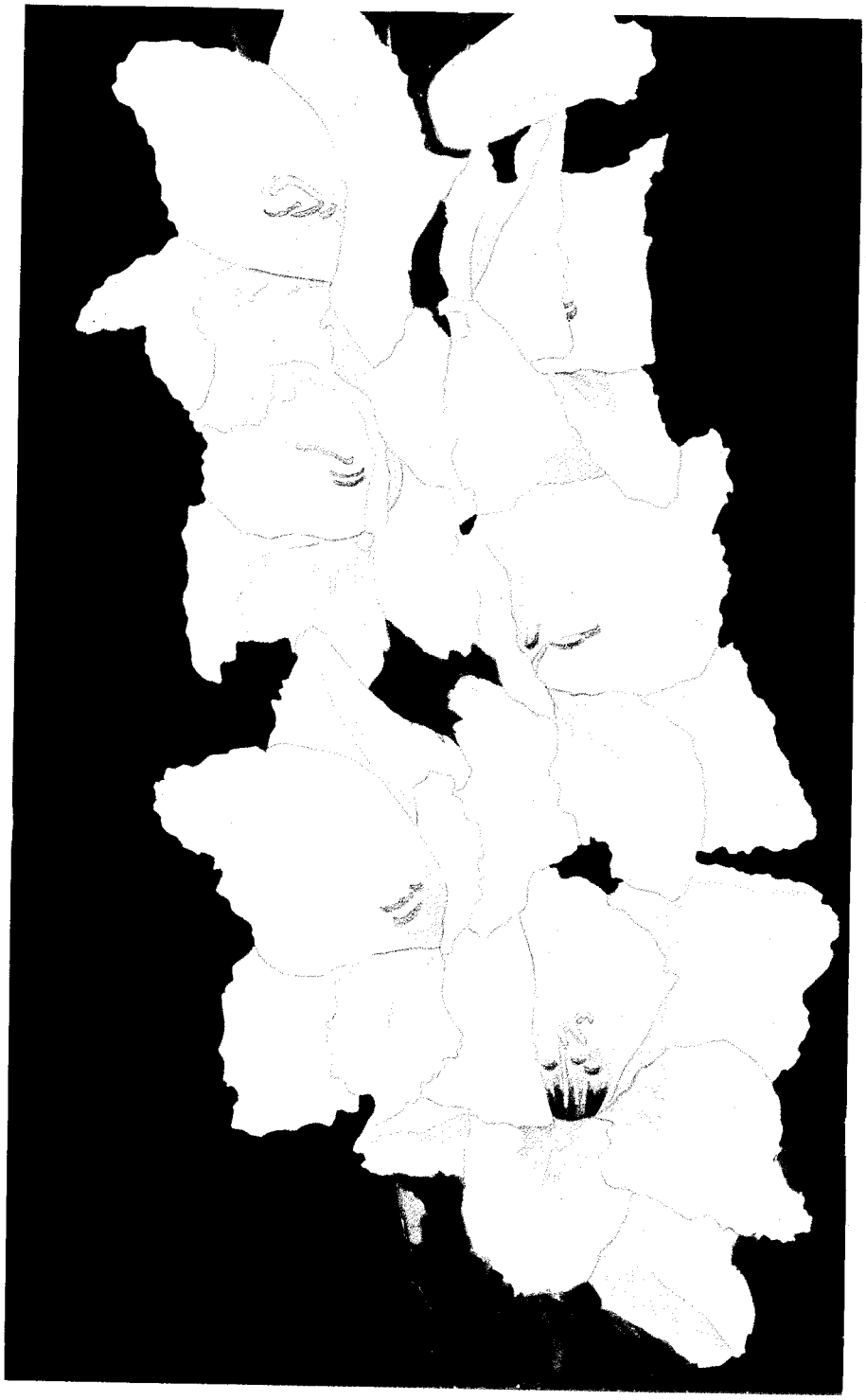
Inventor-Carl Salbach
By Orville M. Kile - Plant Pat. Agt.

Patented Jan. 30, 1940

Plant Pat. 358

UNITED STATES PATENT OFFICE

358

GLADIOLUS

Carl Salbach, Contra Costa County, Calif., assignor to Ella S. Salbach, Contra Costa County, Calif.

Application March 23, 1939, Serial No. 263,749

1 Claim. (Cl. 47—60)

My present invention relates to improvements in flowering gladioli of the type notable for quality of bloom. The object of this invention is to provide a superior variety with large individual flowers of ivory yellow with throat blotch of pink or red, of good quality, placement and form, and with a tall spike.

My new gladiolus originated as a seedling produced by cross pollination work carried on by me. It is a cross between Picardy as the seed parent, and a seedling which was in turn produced by crossing an unnamed seedling with Magna Blanca. This new variety has been asexually reproduced through several generations and its characteristics appear to be permanently fixed.

The illustration accompanying this specification shows a portion of a spike of this variety in approximately their true colors but reduced in size.

Color plate references are to Ridgway's Color Standards and Nomenclature.

Following is a more complete description of the plant and flower of this new variety.

*The plant*

Growth:

Very vigorous. Exceedingly tall, usually growing to a height of sixty inches in my gardens.

Blooming:

Each spike generally has a total of sixteen to eighteen buds and flowers, with six or seven being open at once.

Foliage:

Leaf Green (Plate XLI). Six or seven leaves. Perfectly upright, 12 to 14 inches long. Two lower leaves, others medium width.

Stems:

Stiff and strong and perfectly straight. Almost always two flower stalks to each plant.

Spike:

Spike or flower-head is unusually long, ordinarily being twenty-seven inches from the bottom of the first bloom to the tip of the spike.

Arrangement:

Ideally arranged on spike with all of the flowers facing in the same direction. This variety is consistent in producing this arrangement.

Corms:

Medium in size and usual in appearance.

*The flower*

The blossom:

Consists of six petals.

*Size.*—Individual flowers are exceptionally large for a gladiolus of this type, usually being six inches across.

*Form.*—Flowers are wide-open, somewhat square in form although the tips of the six petals tend to extend in points beyond the square.

*Petals.*—Show a slight fluting and are faintly ruffled at the edges. Substance—very heavy, thus making the variety exceptionally valuable for shipping and for long keeping. Color—the colors in Ridgway which most nearly approach those of my present variety are Ivory Yellow (Plate XXX) with a small throat blotch of Spectrum Red (Plate I), and with an outer blotch or ring of Baryta Yellow (Plate IV).

*Stamens.*—Ivory Yellow. Top of anthers the same but Dark Dull Bluish Violet (Plate XXXV) underneath.

*Pistils.*—Cream Color (Plate XVI). Extend very little farther than stamens.

*Comparison*

Blotched varieties of white to cream or Ivory Yellow are generally very short and have very small blossoms. The variety Solvieg is, at its best, probably the closest approach to my new variety. But it is a very inferior grower that seldom produces good outstanding spikes. The exceptional spikes of Solvieg compare favorably as to size of bloom and height of spike, but the color pattern is different and inferior to my new variety. The variety Solvieg is inconsistent in its growth, while my new variety practically always comes in the good form illustrated and described herein.

The most notable characteristics which in combination readily distinguish my new gladiolus from all other known blotched varieties with cream or Ivory Yellow base, and particularly from the variety Solvieg, are:

1. The exceptional size of flower and height of plant.
2. The unusual, beautiful color combination and pattern.
3. The excellent keeping and shipping qualities.
4. The general symmetry and placement of the flowers.
5. The heavy substance of the flowers.
6. The unusually long flower-head or spike.

Having thus disclosed my invention, I claim:

The new variety of gladiolus herein described and illustrated, characterized particularly by its consistency and vigor of growth, the general symmetry and regular placement of its flowers, its unusually long flower-head, and its exceptionally large flowers having excellent keeping qualities and the novel and beautiful combination of colors as described and shown.

CARL SALBACH.